United States Patent
Sweeney

(10) Patent No.: US 7,344,564 B2
(45) Date of Patent: Mar. 18, 2008

(54) EXPANDABLE SPINAL STABILIZATION DEVICE

(75) Inventor: Patrick J. Sweeney, Flossmoor, IL (US)

(73) Assignee: Spinal Generations, LLC, Olympia Fields, IL (US)

( * ) Notice: Subject to any disclaimer, the term of this patent is extended or adjusted under 35 U.S.C. 154(b) by 530 days.

(21) Appl. No.: 10/863,620

(22) Filed: Jun. 8, 2004

(65) Prior Publication Data

US 2005/0273166 A1    Dec. 8, 2005

(51) Int. Cl.
*A61F 2/44* (2006.01)

(52) U.S. Cl. .................... 623/17.15; 623/17.11

(58) Field of Classification Search ............ 623/17.11, 623/17.15; 606/23, 92, 93, 94
See application file for complete search history.

(56) References Cited

U.S. PATENT DOCUMENTS

| | | | |
|---|---|---|---|
| 4,399,814 | A | 8/1983 | Pratt, Jr. et al. |
| 4,653,489 | A | 3/1987 | Tronzo |
| 4,863,476 | A | 9/1989 | Shepperd |
| 6,048,343 | A | 4/2000 | Mathis et al. |
| 6,126,689 | A | 10/2000 | Brett |
| 6,193,757 | B1 | 2/2001 | Foley et al. |
| 6,210,376 | B1 | 4/2001 | Grayson |
| 6,371,989 | B1 | 4/2002 | Chauvin et al. |
| 6,641,614 | B1 | 11/2003 | Wagner et al. |
| 2001/0032020 | A1 | 10/2001 | Besselink |
| 2002/0010511 | A1 | 1/2002 | Michelson |
| 2002/0022887 | A1 | 2/2002 | Huene |
| 2002/0040243 | A1 | 4/2002 | Attali et al. |
| 2002/0052656 | A1 | 5/2002 | Michelson |
| 2002/0116066 | A1 | 8/2002 | Chauvin et al. |
| 2002/0177897 | A1 | 11/2002 | Michelson |
| 2003/0050701 | A1 | 3/2003 | Michelson |
| 2003/0208270 | A9 | 11/2003 | Michelson |
| 2004/0167626 | A1 | 8/2004 | Geremakis et al. |

OTHER PUBLICATIONS

International Search Report and Written Opinion for PCT/US04/22884; mailed Dec. 10, 2004.

*Primary Examiner*—Corrine McDermott
*Assistant Examiner*—Christopher D. Prone
(74) *Attorney, Agent, or Firm*—Foley & Lardner LLP

(57) ABSTRACT

The present invention relates to an expandable spinal stabilization device that may be inserted into the space between two vertebrae, normally occupied by a disc, in order to stabilize the spine during and after spinal fusion procedures. The invention also relates to a method for using the device. The device generally includes a stack of plates connected by a connecting rod in a manner that allows the plates to adopt a helical configuration about the connecting rod when the plates are rotated about the longitudinal axis of the rod.

20 Claims, 11 Drawing Sheets

EXPANDABLE SPINAL STABILIZATION DEVICE

FIELD OF THE INVENTION

The present invention relates generally to a surgical apparatus for spinal column fusions.

BACKGROUND

It is commonly estimated that about 80% of Americans will see a health care professional at some point in their lives for back problems. While many of these problems can be corrected by exercise and other non-invasive procedures, sometimes surgery is the proscribed corrective measure. A spinal fusion may be the most appropriate treatment for patients suffering from injuries to spinal vertebrae, protrusion and degeneration of the cushioning disc between vertebrae (sometimes called slipped disc or herniated disc), abnormal curvatures (such as scoliosis or kyphosis), and a weak or unstable spine caused by infection or tumor. Spinal fusion has become a common method of correcting spinal problems with about 285,000 spinal fusions performed in 2001.

The spinal column is comprised of twenty six interlocking vertebrae separated by discs. Many times it is the motion between the vertebrae that is the source of the problem or severe pain in the patient. Spinal fusion involves the "welding" of two or more these vertebrae into a single fused bone to limit that motion. After removal of the disc material, the welding is normally done by placing a spacer between the vertebrae and then grafting a bone segment to the vertebrae. The bone for the graft is either taken from elsewhere in the patient (autogenous) or from a bone bank usually consisting of cadaver bone (allograft). Immediate internal bracing, external bracing, and/or casting is then used to support the region until full healing can take place.

SUMMARY OF THE INVENTION

The present invention describes an expandable spinal stabilization device and a method for using such a device for spinal stabilization and fusion procedures.

The device, comprised of a stack of plates attached to a connecting rod, is designed to be inserted between two vertebrae of a spinal column. Prior to and during insertion the device has a minimal radius associated with it, this termed the aligned configuration. The device may then be expanded by turning the plates in the stack about the longitudinal axis of the connecting rod to produce a helical configuration of the plates, the helical configuration having an effective radius greater than that of the radius of the aligned configuration.

Many variations relating to the size and shape of the plates in the device are contemplated. The plate shape, as viewed from a facial orientation can be any of a multitude of shapes including, but not limited to circular, oval, square, star-shaped, triangular, or other multi-sided geometries. The plates may incorporate sharp circumferential edges to provide a way of gripping onto the bone or promoting bone growth, and integrated passages or voids to allow bone growth throughout the device. The device should be constructed of a bio-compatible material.

Another aspect of the invention relates to the incorporation of catches and abutments on the plates to facilitate the formation and retention of the helical configuration. The catches may be either raised from the face of a plate or recessed into the surface of the plates.

Another aspect of the invention relates to a tool for turning the stack of plates into a helical configuration. This aspect utilizes a pair of nested turning sleeves to connect to both the connecting rod of the stack and the top plate of the stack. The inner and/or outer sleeve may be turned to cause the plates to form a helical configuration about the longitudinal axis of the connecting rod.

The invention also is directed to methods for stabilizing and/or fusing a spinal column using the device by insertion of the device, in the aligned configuration, between two vertebrae. The device may be inserted into the intervertebral space using a posterior or posterial lateral approach, posterior to the transverse process. Once in place, the plates of the device may be turned such that the plates adopt the helical configuration. When the device is used to fuse a spine, bone growth-promoting material may be inserted into the intervertebral space around the expandable spinal stabilizing device.

DETAILED DESCRIPTION OF THE INVENTION

Figure 1:
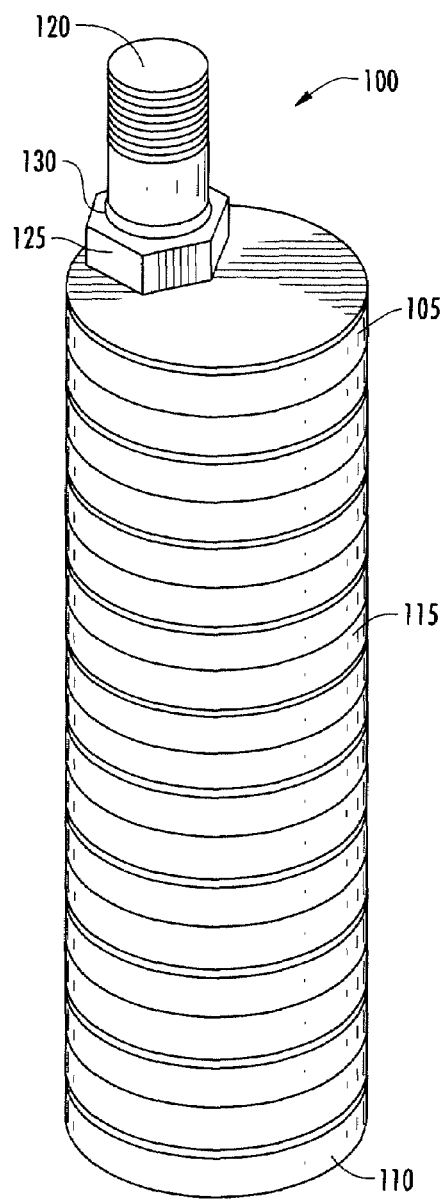
FIG. 1 shows an Expandable Spinal Stabilization Device with the stack of plates in the aligned configuration.

The present invention relates to an expandable spinal stabilization device and a method for using the same. The stabilization device includes a stack of plates joined together by a connecting rod that connects all the plates. When the plates are turned around the longitudinal axis of the connecting rod, catches and abutments on adjacent plates interlock in a manner that forces the plates to adopt a helical configuration about the longitudinal axis of the rod, not unlike a spiral staircase. Through the process of forming a helical configuration of the stack of plates, the effective radius of the device is increased. This allows for insertion of the device between two vertebrae, in the aligned configuration, and then expansion of the device to provide the desired separation of the vertebrae.

In preparing a region of the spine for a stabilization and/or fusion procedure, some or all of the interior contents is located between the vertebrae may be removed and an expandable spinal stabilization device is inserted into the resulting intervertebral space. The surgeon may use one or more of the devices to stabilize the spine in the desired alignment prior to initiating a bone graft that will form the spinal fusion. If dynamic stabilization rather than fusion is desired, the surgeon may also choose to leave the disc in place and insert the device into the disc itself, followed by expansion into the helical configuration.

When used to stabilize or fuse a spinal column, the devices provided herein may be fully or only partially expanded in an intervertebral space. That is, in some applications, the stack of plates will have adopted a helical configuration along the entire length of the stack, while in other applications the stack of plates may have adopted a helical configuration along only a portion of the length of the stack with the remainder of the stack remaining in an aligned or substantially aligned configuration. For the purposes of this disclosure, the devices may be said to have "adopted a helical configuration" when they are in either a fully or partially expanded configuration.

The extent to which the devices provided herein expand upon going from an aligned configuration to a helical configuration will vary depending on such factors as the shapes and sizes of the plates and the rod and the location of the connections between the plates and the rod. In some embodiments, the effective radius of the device increases by at least 20% as it is converted from an aligned configuration to a helical configuration. This includes embodiments where the effective radius of the device increases by at least 30% and further includes embodiments where the effective radius of the device increases by at least 40% as it is converted from an aligned configuration to a helical configuration. However, the invention is not limited to devices that expand to such an extent.

The plates are an integral part of the device. The size and shape of the plates are not their defining characteristics and the shape may vary for different applications or by the preference of the surgeon. However, the size of the plates should be selected to allow the device to be inserted within an intervertebral space, desirably without extending substantially beyond that space. Each plate is characterized by an obverse face (i.e., a face which is turned toward an observer) and an oppositely-facing reverse face. As viewed from the obverse or reverse faces of the plate, the shape may be round, oval, triangular, rectangular, star-shaped, or may have any of a multitude of other multi-sided shapes or geometries that are appropriate for the particular situation. The plates may have sharp circumferential edges, such as blade edges or saw-edges, adapted to decorticate the vertebra as the device is inserted or expanded. The saw-edged shape may be defined as one simulating any of a number of common saw blades commonly used by wood craftsmen in circular or table saws. The sharp, circumferential-edged shape may be defined as having sharp points like the saw-edged shape, a beveled edge like a knife, or a combination thereof. Some of the shapes may be more advantageous in certain situations than others. For example, when a larger effective radius of the device is needed, the oval shape may be more appropriate than the round, or if decortication of the bone is desired to promote bone growth for a fusion, then plates having saw-shaped, or a sharp circumferential edges may be most appropriate. The plates may also have voids, or passages so that when bone growth begins during the fusion process, the new bone may infiltrate the device completely and permanently incorporate it into the spinal column.

The helical configuration is also an integral part of the present invention. The helical configuration may be reminiscent of a screw in shape. The helical shape is adopted by the plates when catches and abutments on adjacent plates engage each other in response to the rotation of the plates about the longitudinal axis of the connecting rod. The abutments and catches may be aligned with, positioned on, and/or connected to the plates in any manner that allows the abutments and catches on neighboring plates to engage when the connecting rod is rotated about its longitudinal axis. Generally, the abutments and catches will be aligned with, positioned on, and/or connected to the reverse and obverse faces of neighboring plates such that they extend away from the face of the plate and toward the space between the plates.

The plates may be connected to the connecting rod in any manner that allows them to adopt a helical configuration. In some embodiments, the rod extends through holes in the plates where the holes are offset from the geometric centers of the plates. In an alternative embodiment, the rod may extend through loops mounted on and extending outwardly from the circumferential edge of each plate. The catches and abutments are desirably disposed on the obverse and reverse faces of the plates and may take on a variety of shapes, sizes, and positions provided they are capable of engaging one another when the plates are rotated about the longitudinal axis of the connecting rod. The plates may be rotated by rotating one of the plates (e.g., the top plate) in the stack, thereby causing the other plates to rotate as their respective catches and abutments become engaged. In other embodiments, the connecting rod is rigidly fixed to one plate in the stack (e.g., the bottom plate) and the plates are rotated by rotating the connecting rod and the plate rigidly attached thereto. In other embodiments, a helical configuration of plates may be achieved by rotating one plate (e.g., the top plate) in one direction and rotating the connecting rod and a plate attached thereto (e.g., the bottom plate) in the opposite direction.

In some embodiments of the device, when an abutment engages a catch, it merely contacts the catch, forcing the plate on which the catch is attached to move in response to the engagement. In other embodiments, the abutment may fit into or even interlock with the catch. Optionally the catch may include a locking mechanism, such as a snap fit, that locks the abutment to the catch when the device is expanded and the helical configuration of plates adopted, preventing an unwanted contraction of the device. In some embodiments, the plates may include more than one catch and/or abutment on their obverse and reverse faces, such that the devices may be expanded from an aligned configuration to a helical configuration by rotating the plates in one direction and then collapsed from its helical configuration back into its aligned configuration by rotating the plates in the opposite direction. For example, a plate may include a forward catch on its obverse (or reverse) face positioned to engage an abutment when the connecting rod in rotated in the clockwise direction and a rearward catch on the same face positioned to engage the abutment when the connecting rod is rotated in the counterclockwise direction.

The device need not be anchored to the bone via screws or other fixation methods as described, for example, by Gerber et al. in U.S. Pat. No. 6,719,794. Instead the device provides support for the vertebrae and optionally serves as a support for the growth of new bone material until the spinal fusion healing process is complete, whereupon it is then part of the spine. The dimensions of the device may be selected such that the compressive force on the device is sufficient to stabilize the device between vertebra, preventing it from slipping out of place. However, the device may optionally include supplemental means of fixation, such as pedicle screws to further secure the device in the intervertebral space.

The device may be constructed from any appropriate, bio-compatible material known to be safe for spinal fusion and grafting procedures. A plethora of such materials are well known. These include, but are not limited to, cobalt chrome, titanium and its many alloys, plastics, ceramics, such as zirconium oxide ceramic and aluminum oxide ceramic, and carbon fiber composites, or other composites. The device may optionally have a coating to assist with bony ingrowth.

Methods for using the devices provided herein are also provided. These methods include the step of inserting a device into an intervertebral space in an aligned (or at least partially aligned) configuration and rotating the connecting rod about its longitudinal axis until the plates adopt a helical configuration (full or partial). The device may be expanded until a stabilizing height is achieved. For example, in some embodiments, the device may be expanded until the patient's natural disc height is restored. In some embodiments, the devices provided herein fuse as well as stabilize the vertebra. In these embodiments, a bone growth-promoting material may be packed around the device after it is implanted in order to facilitate bone growth and fusion. Optionally, the plates in these devices may include pores, channels or other apertures that allow bone growth to permeate the device.

Exemplary embodiments of an expandable spinal stabilization device will now be explained with reference to the figures. This description is provided in order to assist in the understanding of the invention and is not intended to limit the scope of the invention to the embodiments shown in the figures or described below.

Figure 2:
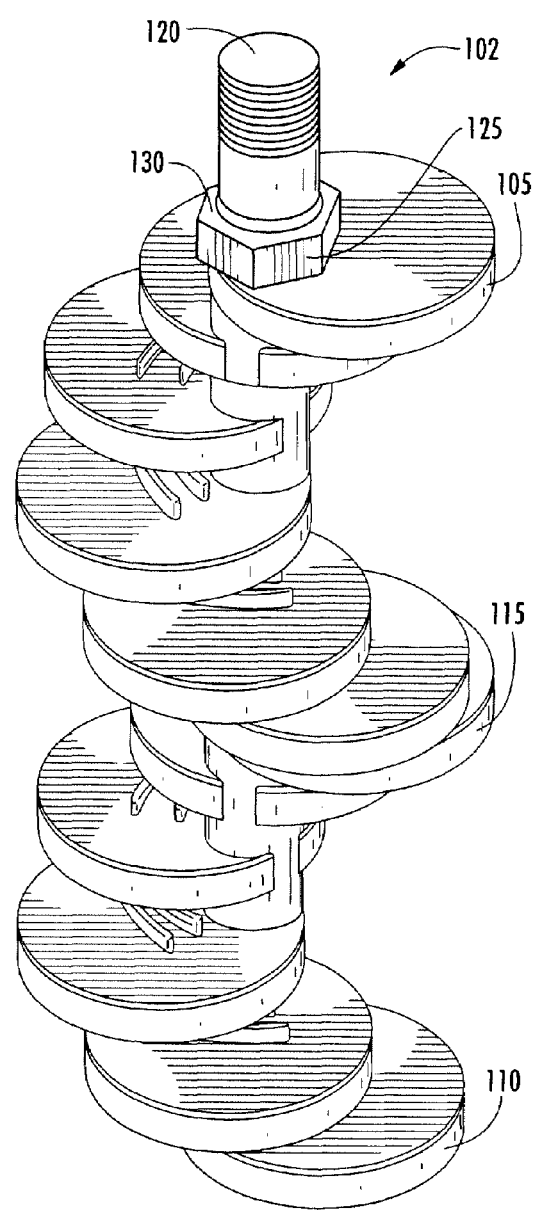
FIG. 2 shows an Expandable Spinal Stabilization Device with the stack of plates in the fully-expanded helical configuration.
Figure 3:
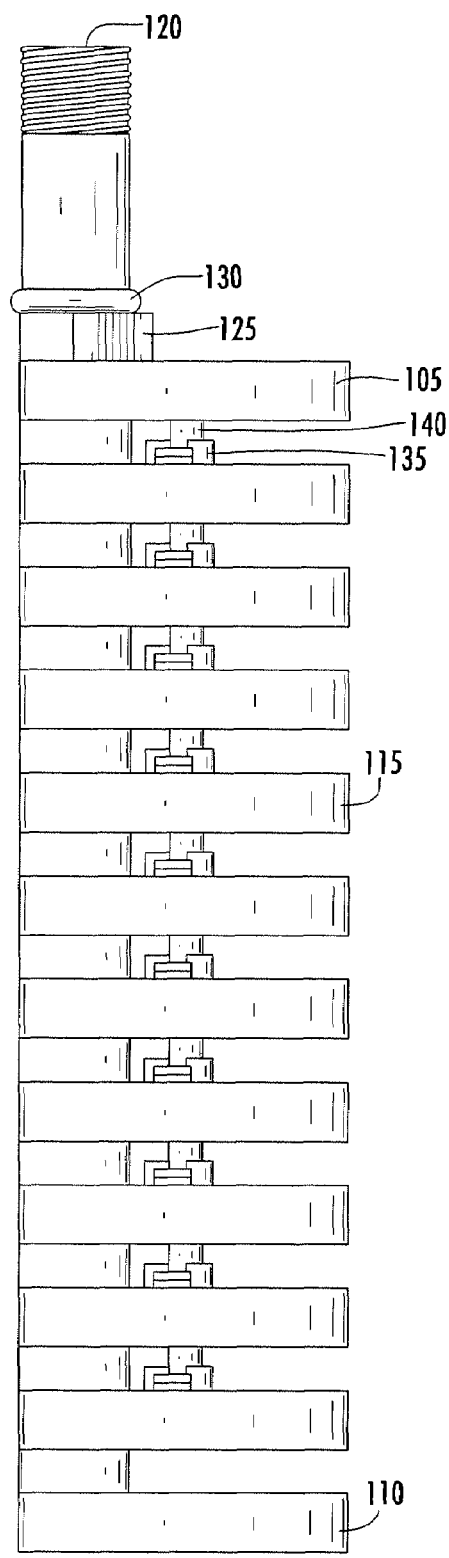
FIG. 3 shows a side view of an Expandable Spinal Stabilization Device with the stack of plates in the aligned configuration.
Figure 4:
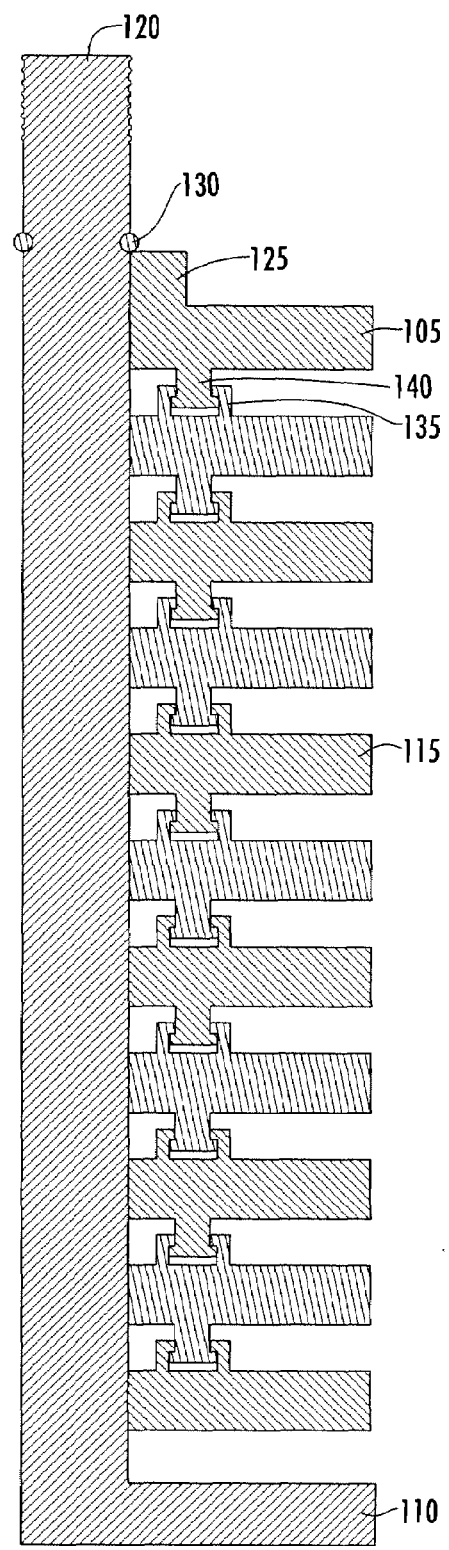
FIG. 4 shows a cross-sectional, side view of the Expandable Spinal Stabilization Device of FIG. 3.
Figure 5A:
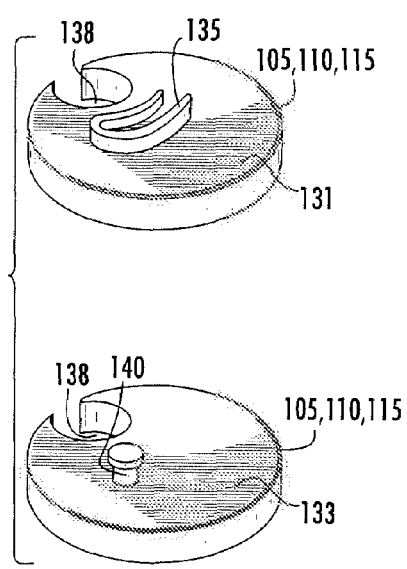
FIG. 5 shows individual plates of the Expandable Spinal Stabilization Device of FIGS. 3 and 4, including a catch and an abutment.
Figure 5B:
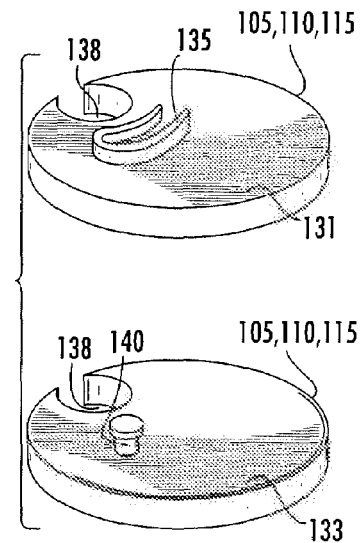
Figure 5C:
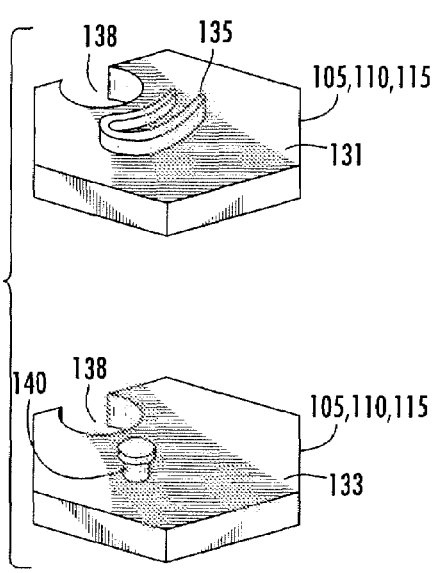
Figure 5D:
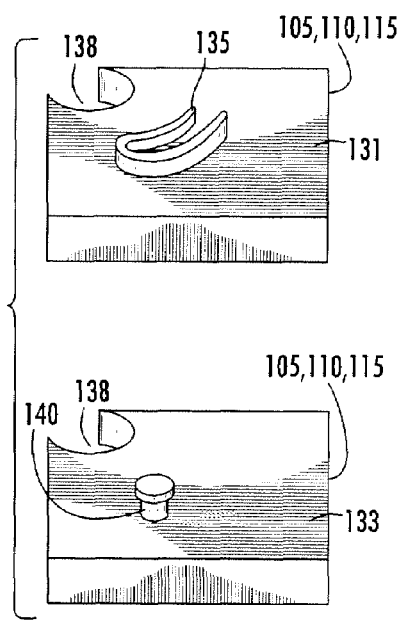
Figure 5E:
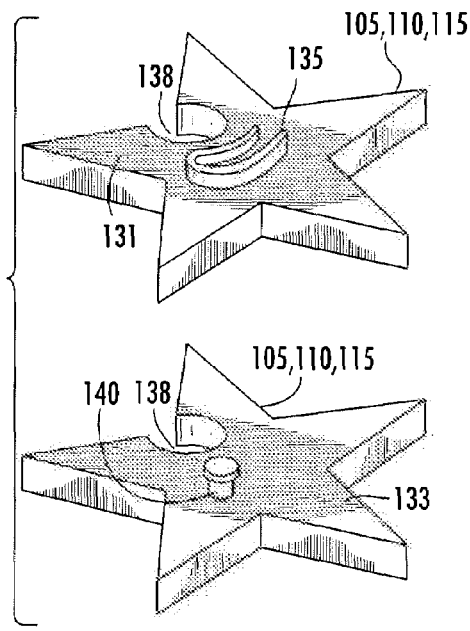
Figure 5F:
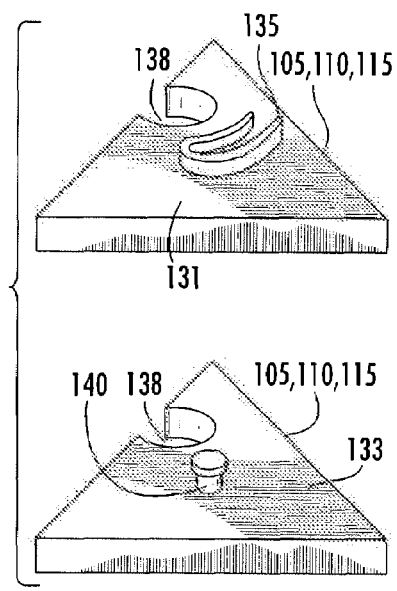
Figure 5G:
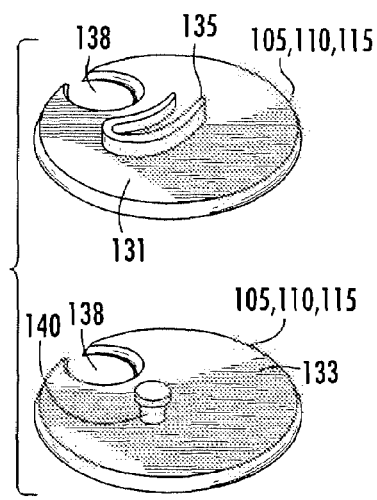
Figure 5H:
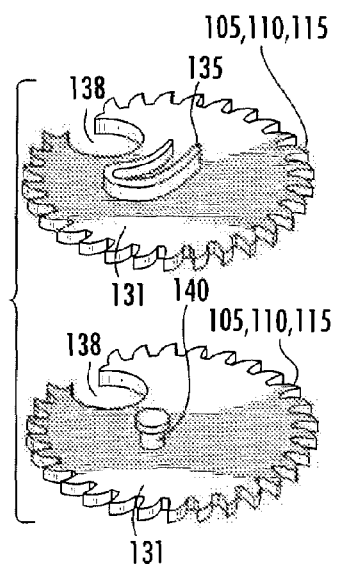
Figure 5I:
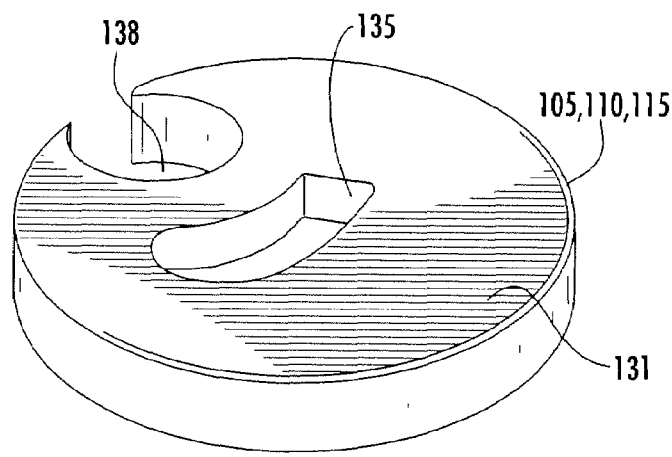

Referring now to FIGS. 1-6, in one embodiment, the expandable spinal stabilization device 100 is constructed from a plurality of plates, including a top plate 105, a bottom plate 110, and a variable number of interstitial plates 115. FIGS. 1 and 2 show perspective views of the device in the aligned and helical configurations, respectively. FIGS. 3 and 4 show side and cross-sectional views of the device of FIG. 1. The variable number of interstitial plates 115 is dependent upon on the length of device 100 needed for the particular patient or region of the spine in which the device 100 will be used. The bottom plate 110 is affixed to the connecting rod 120 so that it cannot move independently of rod 120. The stack is constructed by inserting the connecting rod 120 through holes 138 (shown in FIG. 5), in the plates that are offset from the geometric centers of the plates, but in the same relative location on each plate. The bottom plate of the stack 110 is unable to move independently of the connecting rod 120, while all the other plates 105, 115 may freely turn independent of the connecting rod 120.

FIG. 5 shows more detailed views of two of the plates from the device of FIGS. 1-4. Each plate of the stack has an obverse face and a reverse face and the plates are arranged such that an obverse face of one plate looks at the reverse face of next plate in the stack. In FIG. 5, the upper plate is shown with its obverse face 131 facing upwardly and the lower plate is shown with its reverse face 133 facing upwardly so the viewer can better see both faces. Of course, the obverse face of the top plate and the reverse face of the bottom plate do not have facing, adjacent reverse and obverse faces. In the illustrative embodiment shown in the figures and as best seen in FIGS. 3-7, the obverse face of each plate in the stack, except the top plate, features a catch 135, while the reverse face of each plate in the stack, except the bottom plate and the plate immediately adjacent to the bottom plate, features an abutment 140. As shown here, the catch may take the form of a slot running along the obverse face of the plate in a direction substantially tangential with respect to the connecting rod. In another embodiment, the catch may be recessed as shown in FIG. 5i. The abutment takes the form of a post extending downwardly from the reverse face of its plate. The catches and abutments are positioned on the faces of the plates such that the catch of one plate will engage (e.g., contact or interlock with) the abutment on the adjacent plate, when the stack is rotated. Thus, when the top plate of the stack is turned about the longitudinal axis of the connecting rod, the abutment on the reverse face of the top plate contacts the catch on the obverse face of the second plate. The abutment on the reverse face of the second plate then contacts the catch on the obverse face of the third plate. This series may be continued until all catches and abutments have been engaged and the stack achieves a helical configuration. The plates may have various shapes, including for example, circular (FIG. 5a), oval (FIG. 5b), multi-sided (FIG. 5c), square (FIG. 5d), star-shaped (FIG. 5e), triangular (FIG. 5f), and saw-shaped (FIG. 5h). Further, the plates may have sharp cutting edges on the circumferential edges (FIG. 5g).

It should be understood that although the abutments in the embodiment depicted in the figures are disposed on the reverse faces of the plates and the catches are disposed on the obverse faces, alternative constructions are possible. For example, the abutments may be disposed on the obverse faces and the catches on the reverse faces. In other embodiments, some plates may have abutments on both faces or catches on both faces, provided that at least one abutment and at least one catch is disposed between adjacent pairs of plates in the stack.

Figure 6:
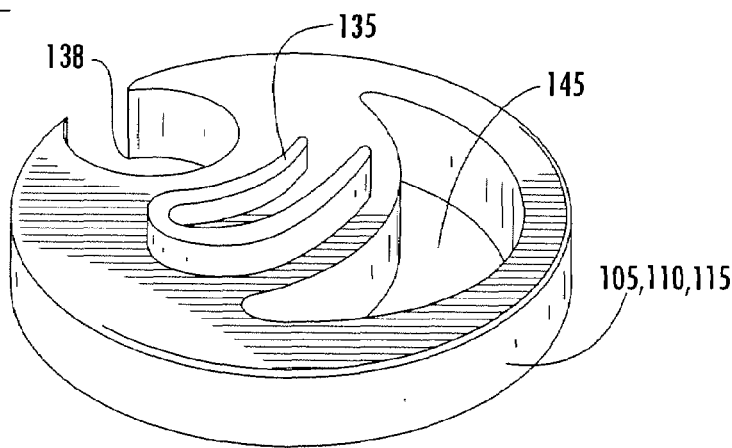
FIG. 6 shows individual plates having voids for the insertion of bone growth-promoting materials.
Figure 6:
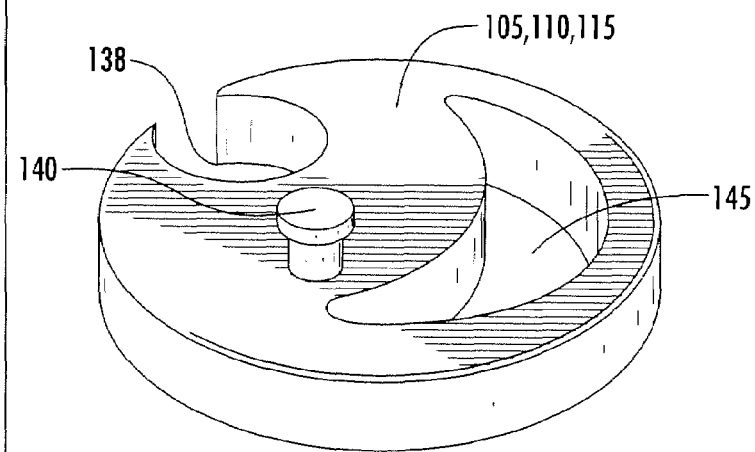

FIG. 6 depicts a variation of the plates of FIG. 5 where the plates include a channel 145 into which a bone-growth promoting material may be deposited and through which the vertebra may develop a fusion.

Figure 7:
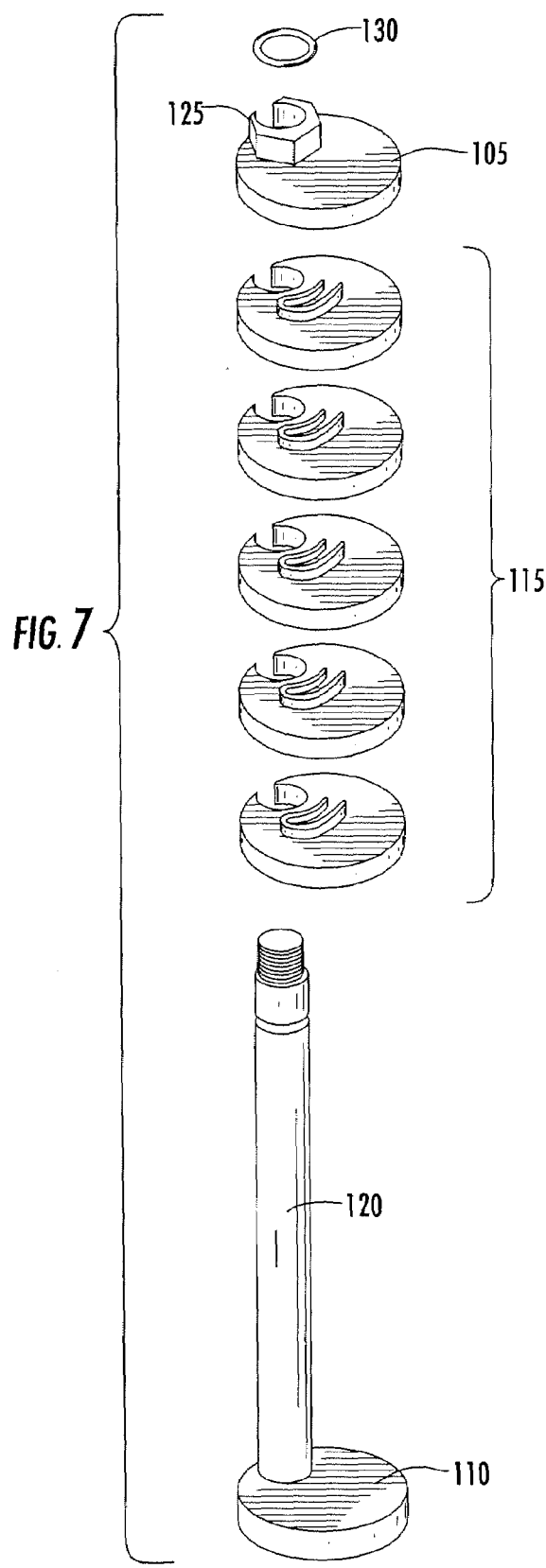
FIG. 7 shows the stack of plates of FIGS. 3 and 4 removed from the connecting rod.

FIG. 7 shows a perspective view of the device with the top 105 and interstitial 115 plates removed from the connecting rod 120.

Figure 8:
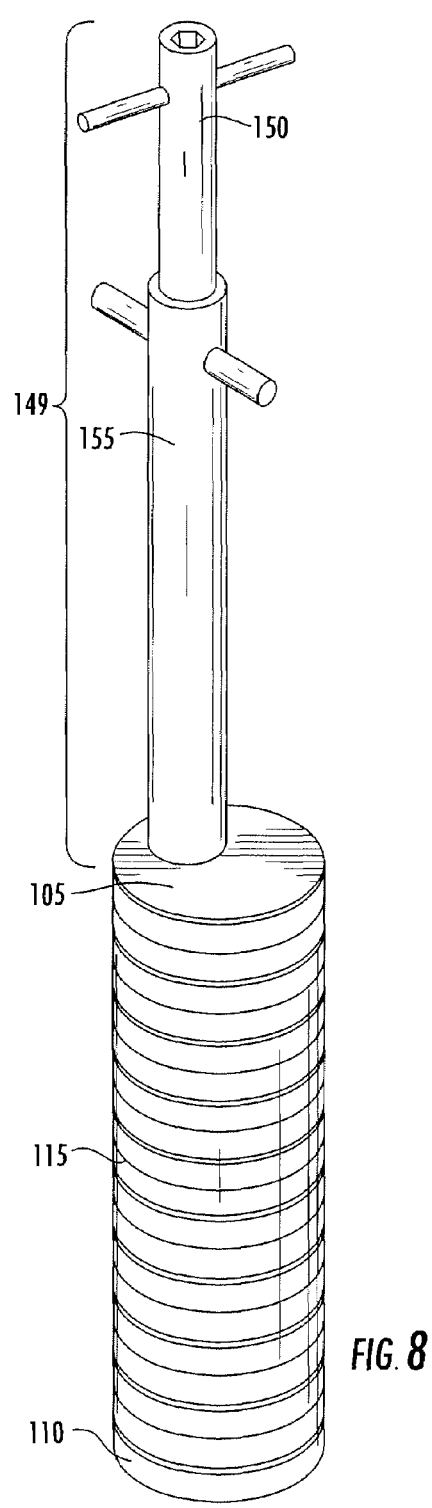
FIG. 8 shows an Expandable Spinal Stabilization Device in the aligned configuration along with a turning tool.
Figure 9:
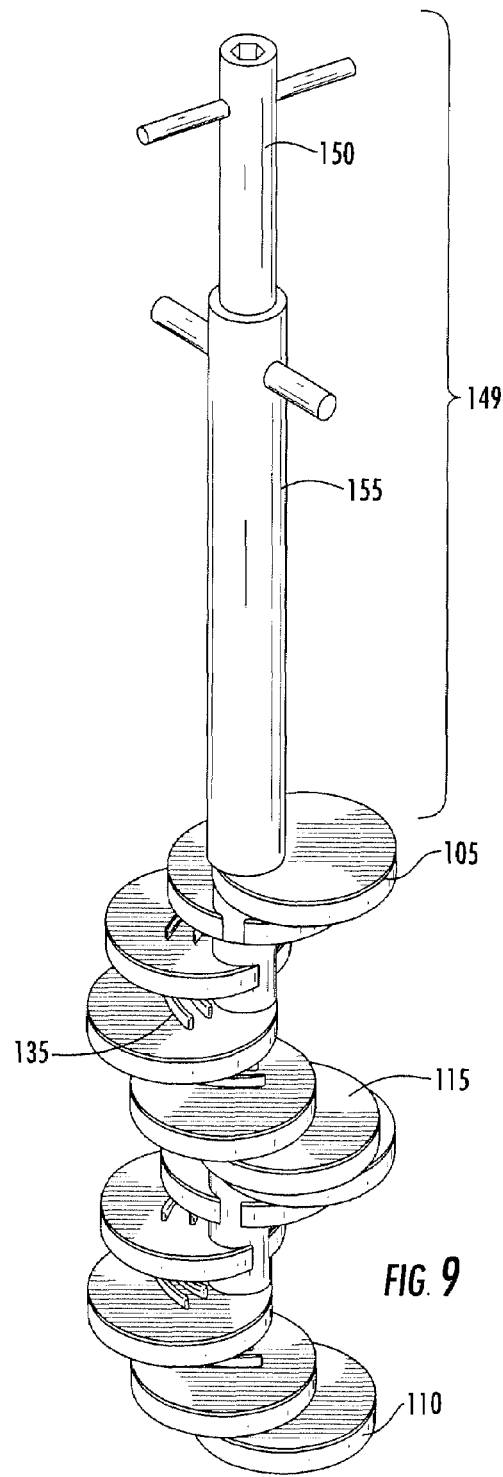
FIG. 9 shows an Expandable Spinal Stabilization Device in the helical configuration along with a turning tool.
Figure 10:
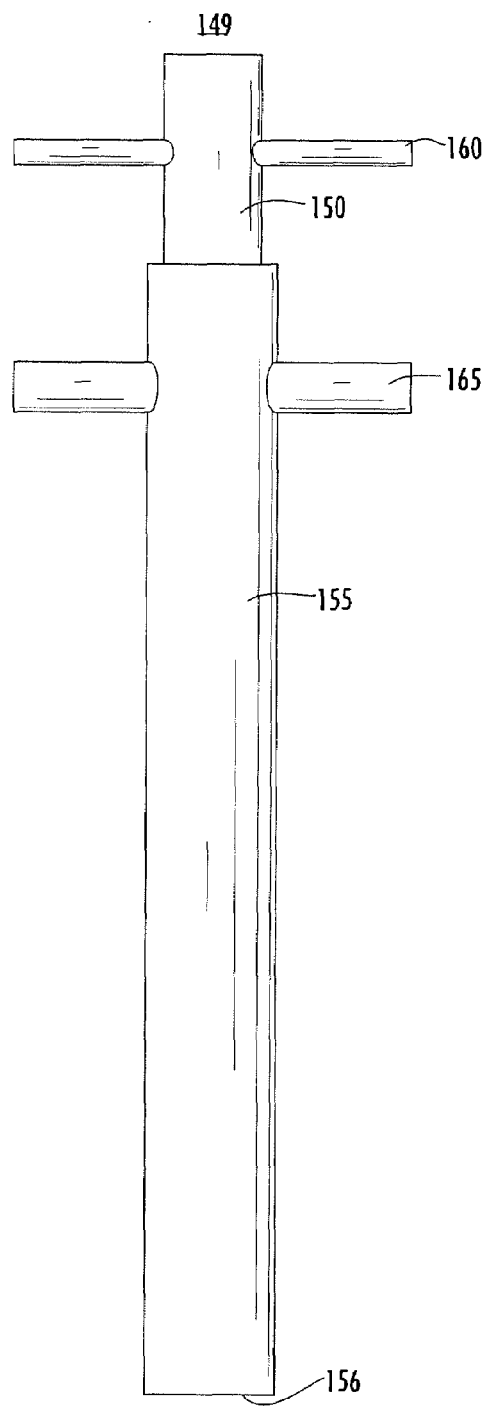
FIG. 10 is a view of the nested turning sleeves of the turning tool shown in FIGS. 8 and 9.
Figure 11:
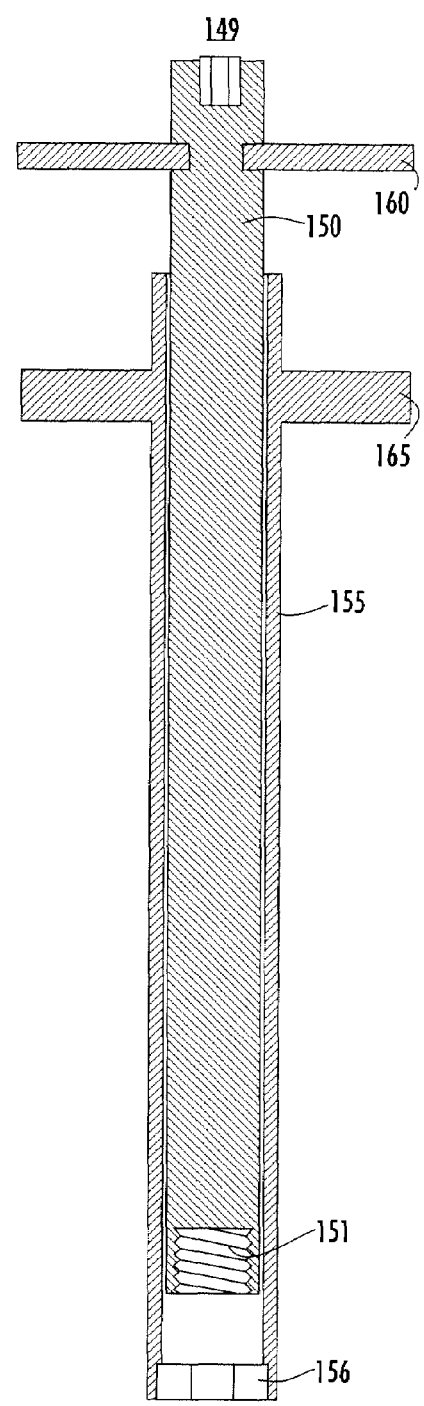
FIG. 11 is a cross-sectional view of the turning tool of FIG. 10.
Figures 12A, 12B, 12C:
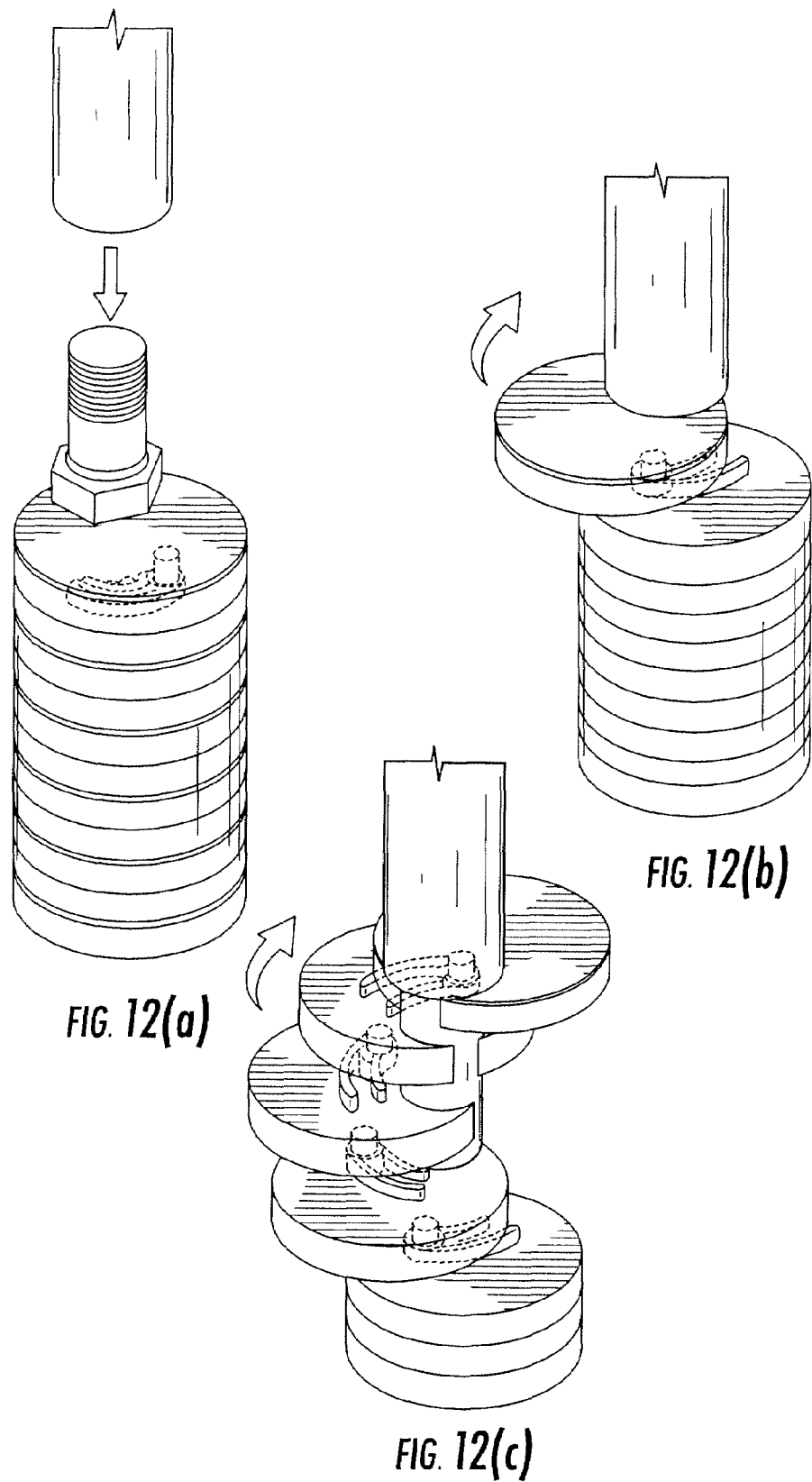
FIG. 12 is a stepwise representation of (a) the turning sleeves engaging the device, (b) the turning of the top plate, and (c) the subsequent turning of the remainder of the plates in the stack of plates.

As shown in FIGS. 8, 9, and 12, the top plate 105 may be turned, or rotated, using a turning tool 149. The turning tool, shown in FIGS. 10 and 11 includes an outer sleeve 155 having one end 156 that is adapted to engage a sleeve connector 125 on the obverse face of the top plate 105. As shown in the figure, the sleeve connector 125 may take the form of a nut and the end 156 of the outer sleeve 155 may define an opening shaped to fit over and engage the nut. A retaining member (e.g., a retaining ring) 130 may be placed over the sleeve connector 125 to hold the stack of plates in place on the connecting rod 120. The turning tool 149 also includes an inner sleeve 150 nested within outer sleeve 155. The inner sleeve 150 has one end 151 adapted to engage the end of the connecting rod 120 extending beyond the top plate 105. As shown in the figures, the end of the connecting rod 120 extending upwardly beyond the top plate 105 of the stack may be threaded and the end 151 of the inner sleeve may define a threaded bore adapted to engage the threaded end of the connecting rod 120. Both sleeves may optionally include handles 160, 165. The outer sleeve 155 may be turned to produce a helical configuration of plates along the stack. This action is pictorially summarized in FIGS. 12a-12c.

Figure 14:
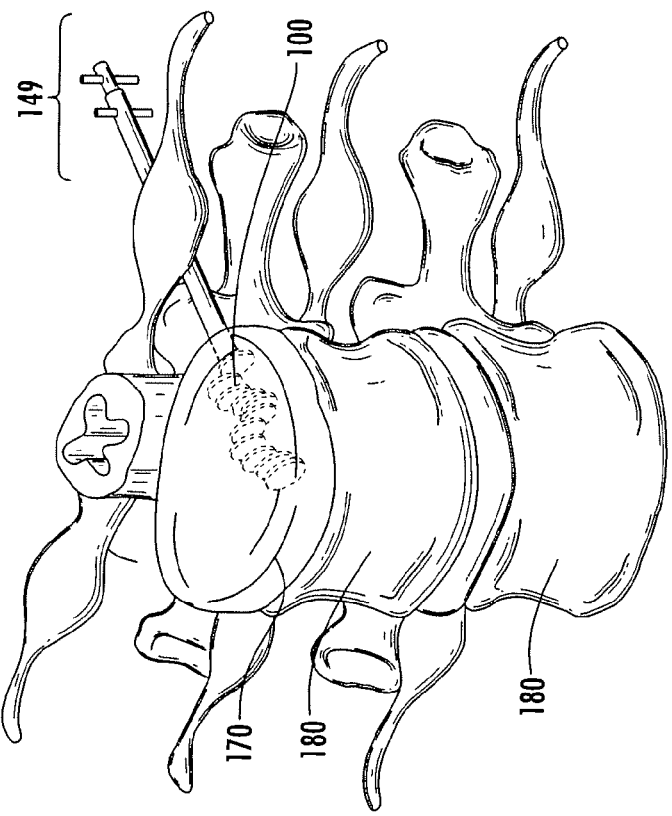
FIG. 14 shows an Expandable Spinal Stabilization Device, in the helical configuration, inserted into the intervertebral space between two vertebrae of a spine.
Figure 13:
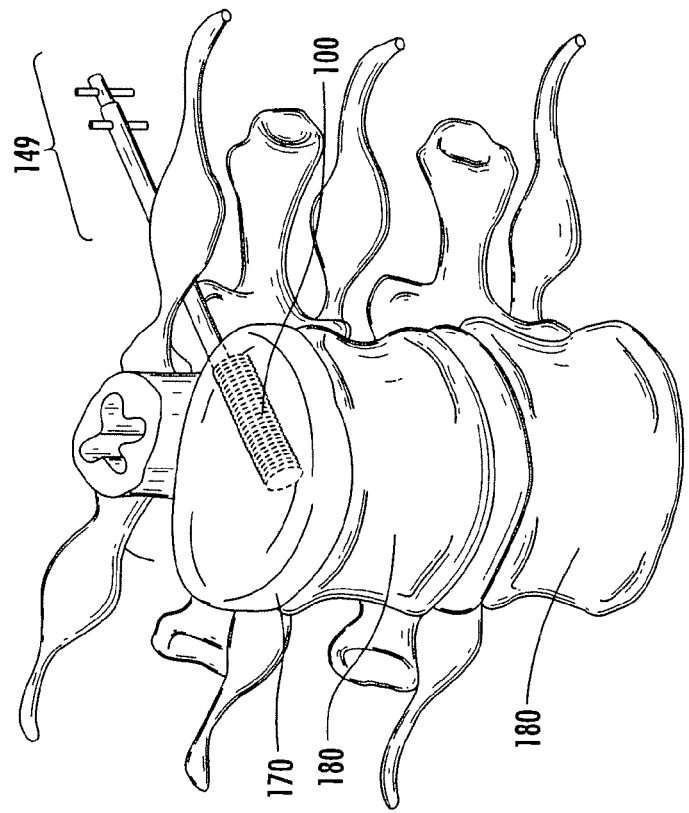
FIG. 13 shows an Expandable Spinal Stabilization Device, in the aligned configuration, inserted into the intervertebral space between two vertebrae of a spine.
Figure 15:
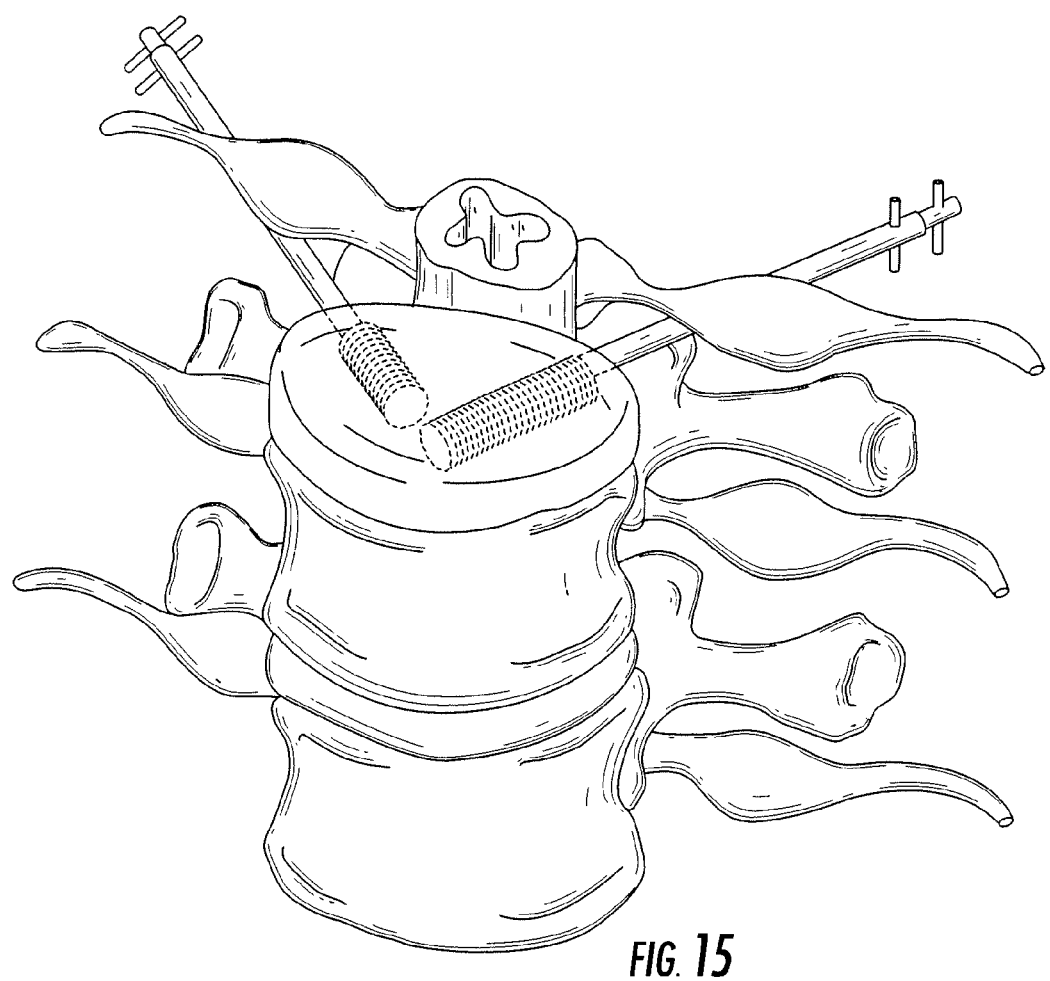
FIG. 15 shows multiple Expandable Spinal Stabilization Devices, in the aligned configuration, inserted into the intervertebral space between two vertebrae of a spine.

Another embodiment of the invention is directed at a method for using the device 100 in a spine. As depicted in FIGS. 13-15, the device 100 is inserted into the disc region 170 located between vertebra 180 in a spinal column in an aligned configuration (FIG. 13). The turning tool 149 is then used to expand the device 100 into the desired helical configuration (FIG. 14), after which the turning tool may be removed. Multiple devices 100 may be used to stabilize both sides of the spine or to stabilize both posterior (rear) and anterior (frontal) sides of the spine (FIG. 15). As shown in FIGS. 13-15, the devices may be inserted into an intervertebral space using a posterior or posterial lateral approach, posterior to the transverse process. However, other approaches, such as an anterior approach, may also be used. Optionally, a tube or cannula may be used to protect surrounding tissue during the insertion of the device.

A plethora of variations on the general theme of the above embodiments are contemplated, such as the ordering of the catches and abutments on the obverse and reverse faces of the plates of the stack. Therefore, in another embodiment, arrangements of catches and abutments may be described in the more generic manner that follows. Each plate of the stack has an obverse face and a reverse face and the plates are arranged such that an obverse face of one plate looks at the reverse face of next plate in the stack. Each face of a plate in the stack features either a catch or an abutment with the catches and abutments arranged on the obverse and reverse faces of the plates in a manner such that for each catch there is an abutment on the adjacent face of the next plate in the stack. The ordering of the catches and abutments is immaterial as long as for every catch there is an abutment on the adjacent face of the next plate in the stack. Thus, one plate may have two catches as long as the two adjacent faces to that plate have abutments that may be contacted by the catches. In FIGS. 2-6, the catches are depicted as slots 135, raised from the face of the plates 110, 115. However, it is also apparent that the slots may be recessed into the plates to provide the same function. The abutments are depicted as posts 140 and are shown on the reverse face of the plates 105, 115, while the slots are shown on the obverse face of plates 110, 115. However, it is also apparent that the posts may reside on the obverse face of plates 110, 115, while the slots are on the reverse face of plates 105, 115. While it is not an object of this invention to recite all the combinations of catches and abutments, it is contemplated that those features may be arranged on the plates in any manner such that any given structure, catch or abutment, has the complementary structure on the adjacent facing plate.

FIG. 6 details the use of other voids or passages 145 in the plates as a region through which bone growth may occur. Other contemplated embodiments would have the plates constructed from very porous, bio-compatible substances that would allow bone growth throughout the plate structure allowing for fusion of the spinal column.

It should be understood that various changes and modifications to the embodiments described herein would be apparent to those skilled in the art. Such changes and modifications can be made without departing from the spirit and scope of the present invention. It is, therefore, intended that such changes and modifications be covered by the appended claims.

What is claimed is:

1. An expandable spinal stabilization device comprising:
a plurality of plates arranged in a stack comprising a top plate, a bottom plate, and one or more interstitial plates disposed between the top plate and the bottom plate, each plate comprising an obverse face and a reverse face such that a pair of adjacent faces comprising the obverse face of one plate and the reverse face of an adjacent plate is provided for each pair of adjacent plates in the stack, wherein:
  a. one face in at least one pair of adjacent faces comprises a catch;
  b. the other face in the at least one pair of adjacent faces comprises an abutment; and further wherein
  c. the abutment is positioned in a manner to engage the catch of an adjacent face when the plates are rotated about the longitudinal axis of a connecting rod connecting the plurality of plates; wherein the plates are connected to the connecting rod such that the plurality of plates adopt a helical configuration about the longitudinal axis of the connecting rod when the plates are turned about the longitudinal axis of the connecting rod; and further wherein the dimensions of the device render it suitable for insertion into an intervertebral space.

2. The device according to claim 1 wherein the plurality of plates comprise a top plate, a bottom plate, and one or more interstitial plates disposed between the top plate and bottom plate, each plate comprising an obverse face and a reverse face, further wherein the connecting rod extends through the obverse and reverse faces of the top plate and the interstitial plates at a position offset from the geometric center of the plates.

3. The device according to claim 1 wherein the plates are circular.

4. The device according to claim 1 wherein the plates are oval.

5. The device according to claim 1 wherein the circumferential edges of the plates are multi-sided.

6. The device according to claim 5 wherein the plates are square.

7. The device according to claim 5 wherein the plates are star-shaped.

8. The device according to claim 5 wherein the plates are triangular.

9. The device according to claim 1 wherein the circumferential edges of the plates provide sharp cutting edges.

10. The device according to claim 9 wherein the plates are saw-shaped.

11. The device according to claim 1 wherein the plates and the connecting rod are comprised of a biocompatible material.

12. The device according to claim 1 wherein the plates have integrated passages.

13. The device according to claim 1 wherein one face in every pair of adjacent faces except the final pair comprises a catch and the other face in every pair of adjacent faces except the final pair comprises an abutment.

14. The device according to claim 1 wherein the reverse face of each pair of adjacent faces comprises an abutment and the obverse face of the at least one pair of adjacent faces comprises a catch.

15. The device according to claim 1 wherein each catch comprises a slot running along the obverse or reverse face of a plate in a direction substantially tangential with respect to the circumference of the connecting rod and each abutment comprises a post extending away from the obverse or reverse face of a plate.

16. The device according to claim 15 wherein the slots are raised from the obverse or reverse faces of the plates.

17. The device according to claim 15 wherein the slots are recessed in the obverse or reverse faces of the plates.

18. The device according to claim 1 wherein the bottom plate is unable to move independently of the connecting rod and the top plate and interstitial plates are connected to the connecting rod in a manner that allows them to rotate about the longitudinal axis of the connecting rod.

19. The device according to claim 18 wherein the obverse face of the top plate comprises a sleeve connector disposed thereon and the connecting rod comprises an end extending beyond the obverse face of the top plate, the device further comprising a turning tool, the turning tool comprising:
   a. an outer sleeve having an end adapted to engage the sleeve connector; and
   b. an inner sleeve nested within the outer sleeve, the inner sleeve having an end adapted to engage the end of the connecting rod extending beyond the top plate such that when the inner sleeve engages the connecting rod and the outer sleeve engages the sleeve connector, the helical configuration is achieved by turning at least one of the inner and outer sleeves.

20. The device according to claim 19 wherein the sleeve connector is a nut and the end of the outer sleeve is adapted to engage the nut, and further wherein the end of the connecting rod extending beyond the top plate is threaded and the end of the inner sleeve is adapted to engage the threads.

* * * * *